(12) United States Patent
Schaefer et al.

(10) Patent No.: US 11,767,493 B2
(45) Date of Patent: Sep. 26, 2023

(54) BLEACH ACTIVATOR HAVING A CATIONIC GROUP AND WASHING OR CLEANING AGENT CONTAINING SAME

(71) Applicant: Henkel AG & Co. KGaA, Duesseldorf (DE)

(72) Inventors: Sascha Schaefer, Duesseldorf (DE); Svenja Neuhaus, Duesseldorf (DE); Antje Gebert-Schwarzwaelder, Duesseldorf (DE); Christa Junkes, Duesseldorf (DE); Arne Jansen, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 17/749,520

(22) Filed: May 20, 2022

(65) Prior Publication Data
US 2022/0275310 A1 Sep. 1, 2022

Related U.S. Application Data

(63) Continuation of application No. PCT/EP2020/082198, filed on Nov. 16, 2020.

(30) Foreign Application Priority Data

Nov. 20, 2019 (DE) .................... 102019217851.0

(51) Int. Cl.
| | | |
|---|---|---|
| C11D 3/20 | (2006.01) | |
| C11D 3/28 | (2006.01) | |
| C11D 3/395 | (2006.01) | |
| C11D 3/39 | (2006.01) | |
| C07D 207/27 | (2006.01) | |
| C07D 223/10 | (2006.01) | |
| C11D 11/00 | (2006.01) | |
| C11D 3/30 | (2006.01) | |
| C11D 7/32 | (2006.01) | |
| C11D 7/26 | (2006.01) | |
| B08B 3/08 | (2006.01) | |
| B08B 3/10 | (2006.01) | |
| D06L 1/04 | (2006.01) | |

(52) U.S. Cl.
CPC .............. *C11D 3/3927* (2013.01); *B08B 3/08* (2013.01); *B08B 3/10* (2013.01); *C07D 207/27* (2013.01); *C07D 223/10* (2013.01); *C11D 3/2096* (2013.01); *C11D 3/28* (2013.01); *C11D 3/30* (2013.01); *C11D 3/391* (2013.01); *C11D 3/392* (2013.01); *C11D 3/3942* (2013.01); *C11D 3/3947* (2013.01); *C11D 3/3951* (2013.01); *C11D 3/3953* (2013.01); *C11D 3/3956* (2013.01); *C11D 7/267* (2013.01); *C11D 7/3209* (2013.01); *C11D 7/3281* (2013.01); *C11D 11/0017* (2013.01); *C11D 11/0023* (2013.01); *D06L 1/04* (2013.01)

(58) Field of Classification Search
CPC .......... C11D 3/2096; C11D 3/28; C11D 3/30; C11D 3/391; C11D 3/392; C11D 3/3927; C11D 7/267; C11D 7/3281; C11D 7/3209; B08B 3/08; B08B 3/10; D06L 1/04
USPC ............... 510/220, 224, 312, 376, 500, 505; 134/25.2; 8/111, 137
See application file for complete search history.

(56) References Cited

U.S. PATENT DOCUMENTS

| | | | | |
|---|---|---|---|---|
| 2008/0261852 A1* | 10/2008 | Schirmer-Ditze | ... | C11D 3/3927 510/311 |
| 2012/0289449 A1* | 11/2012 | Adamy | ................ | C11D 3/3932 510/372 |

FOREIGN PATENT DOCUMENTS

| | | |
|---|---|---|
| CN | 104151310 A | 11/2014 |
| EP | 0816336 A1 | 7/1998 |
| WO | 9606915 A1 | 3/1996 |
| WO | 2017102475 A1 | 6/2017 |

OTHER PUBLICATIONS

Wang et al. Synthesis, Characterization, and Toxicological Properties of New Cationic Bleach Activators,J. Surfact Deterg (2017) 20, 2077-285.

Lim, Gursoy, Hauser, Hinks, Performance of a New Cationic Bleach Activator on a Hydrogen Peroxide Bleaching System, Color. Technol., 120 (2004), 114-118.

PCT International Search Report PCT/EP2020/082198 Completed: Feb. 1, 2021; dated Feb. 9, 2021 5 pages.

\* cited by examiner

*Primary Examiner* — Gregory R Delcotto
(74) *Attorney, Agent, or Firm* — P. Scott Smith

(57) ABSTRACT

The present invention relates to compounds which form, under perhydrolysis conditions, certain cationic organic peracids, to the use of said compounds for activating peroxygen compounds in the context of bleaching stains when washing textiles and cleaning hard surfaces, and to washing and cleaning agents that contain said compounds.

20 Claims, No Drawings

BLEACH ACTIVATOR HAVING A CATIONIC GROUP AND WASHING OR CLEANING AGENT CONTAINING SAME

FIELD OF INVENTION

The present invention relates to compounds which form, under perhydrolysis conditions, certain cationic organic peracids, to the use of said compounds for activating peroxygen compounds in the context of bleaching stains when washing textiles and cleaning hard surfaces, and to washing and cleaning agents that contain said compounds.

BACKGROUND

Inorganic peroxygen compounds, in particular hydrogen peroxide and solid peroxygen compounds which dissolve in water with release of hydrogen peroxide, such as sodium perborate and sodium carbonate perhydrate, have long been used as oxidizing agents for disinfection and bleaching purposes. The oxidizing effect of these substances depends greatly on temperature in dilute solutions; for example, with $H_2O_2$ or alkali perborate in alkaline bleaching liquors, sufficiently rapid bleaching of stained textiles is only achieved at temperatures above approximately 80° C. At lower temperatures, the oxidizing effect of the inorganic peroxygen compounds can be improved by the addition of what are referred to as bleach activators, which are capable of yielding peroxycarboxylic acids under the above-mentioned perhydrolysis conditions and have become known in the literature for numerous proposals, especially from the substance classes of N- or O-acyl compounds, for example polyacylated alkylenediamines, in particular tetraacetylethylenediamine, acylated glycolurils, in particular tetraacetylglycoluril, N-acylated hydantoins, hydrazides, triazoles, hydrotriazines, urazoles, diketopiperazines, sulfurylamides and cyanurates, also carboxylic acid anhydrides, in particular phthalic acid anhydride and alkyl succinic acid anhydrides, carboxylic acid esters, in particular sodium nonanoyl oxybenzenesulfonate, sodium isononanoyl oxybenzene sulfonate, O-acylated sugar derivatives such as pentaacetyl glucose, and N-acylated lactams, such as N-benzoylcaprolactam. By adding these substances, the bleaching effect of aqueous peroxide liquors can be increased to such an extent that said liquors produce substantially the same effects at temperatures as low as approximately 60° C. as those produced with the peroxide liquor alone at 95° C.

With a view to obtaining energy-saving washing and bleaching processes, application temperatures significantly below 60° C., in particular below 45° C. down to cold water temperature, have become increasingly important in recent years.

At low temperatures, the effect of previously known activator compounds generally diminishes to a noticeable extent.

International patent application WO 96/06915 A1 discloses bleach activators which, under perhydrolysis conditions, form organic peroxoacids having a cationic group.

SUMMARY OF THE INVENTION

Surprisingly, it has now been found that compounds which form, under perhydrolysis conditions, organic peroxoacids having a cationic group and in which a quaternary N atom is part of a heterocyclic 6-membered functional group are particularly suitable for enhancing the bleaching effect of washing and cleaning agents containing peroxygen.

DETAILED DESCRIPTION OF THE INVENTION

The invention therefore relates to a bleach-activating compound of general formula (I)

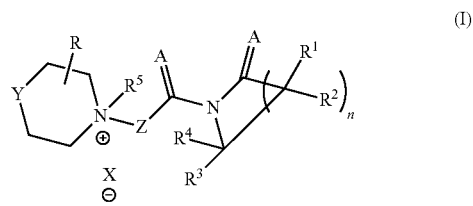

in which
A represents O, S or Se;
Z represents an optionally substituted C1-30 alkylene, C3-30 cycloalkylene, arylene, alkylenearylene or arylenealkylene functional group;
X- represents an anion, in particular chloride, bromide, iodide, tosylate, mesylate, triflate, sulfate, carbonate and/or phosphate;
Y represents NR6, O, S or Se; R, R1, R2, R3, R4, R5 and R6 represent, independently of one another, H, a C1-30 alkyl, C3-30 cycloalkyl, aryl, alkylaryl or arylalkyl functional group; and n represents a number in the range of from 1 to 12.

In the specified hydrocarbon functional groups, 1 or more non-adjacent carbon atoms not bonded to a heteroatom can be replaced by a heteroatom, in particular N, O, S and/or Se. If X- is a polyvalent anion, a plurality of the units which form the remaining part of the compound according to formula (I) and contain the cationic heterocycle are correspondingly present for each anion X-. R, R1, R2, R3, R4, R5 and/or R6 are preferably H, and/or A is preferably O, and/or n is preferably at least 2 and in particular a number in the range of from 2 to 4. As shown in the following formula (II), Z is preferably derived from an optionally substituted alkylbenzene unit in which a C atom of the aromatic ring is bonded to the unit C=A, a C atom of the alkyl functional group is bonded to the shown N atom of the six-membered heterocycle, and the methyl group is the preferred alkyl functional group:

For the compounds of formula (II), the definitions given for formula (I) for A, n, R and R1 to R5, Y and X- likewise apply; R', R9 and R10 represent, independently of one another, H, a C1-30 alkyl, C3-30 cycloalkyl, aryl, alkylaryl or arylalkyl functional group, it also being possible, in these functional groups, to replace 1 or more non-adjacent carbon atoms not bonded to a heteroatom with a heteroatom, in particular N, O, S and/or Se. R', R9 and/or R10 are preferably H.

The invention further relates to the use of compounds of general formula (I) for enhancing the cleaning performance of peroxygen-containing and in particular surfactant-containing washing or cleaning agents in an aqueous liquor.

The use according to the invention consists substantially in creating conditions under which the peroxygen compound and the compound of general formula (I) can react with one another, with the aim of obtaining secondary products having a stronger oxidizing effect. Such conditions exist in particular when the reaction partners come together in an aqueous system. This can be achieved by separately adding the peroxygen compound and the compound of general formula (I) to a liquor which optionally contains a washing or cleaning agent. However, this is particularly advantageously achieved using a washing or cleaning agent which contains the compound of formula (I) and a peroxidic oxidizing agent. The peroxygen compound can also be added separately, in bulk or as a preferably aqueous solution or suspension, to the aqueous system if a washing or cleaning agent is used that does not contain any peroxygen compounds. Depending on the intended use, the conditions can be varied to a high degree. For example, in addition to purely aqueous solutions, mixtures of water and suitable organic solvents can also be used as the reaction medium.

The invention further relates to a method for washing laundry and a method for cleaning hard surfaces, comprising the method steps of (a) providing an aqueous liquor containing H2O2 or an in particular inorganic peroxygen compound which yields H2O2 in water and a compound according to general formula (I), and (b) bringing this liquor into contact with textiles to be washed or hard surfaces to be cleaned. The contact between the aqueous liquor and the object to be washed or cleaned is preferably made at temperatures in the range of from 20° C. to 40° C., in particular from 20° C. to 30° C. The object to be washed or cleaned preferably remains in contact with the aqueous liquor for a period of from 20 minutes to 120 minutes, in particular from 30 minutes to 90 minutes. The methods according to the invention can be carried out manually or with the aid of conventional devices, for example washing machines or dishwashers. In the context of the use according to the invention and a method according to the invention, the use amounts of peroxygen compounds are generally selected such that between 10 ppm and 10% active oxygen, preferably between 50 ppm and 5,000 ppm active oxygen, is present in the liquor.

A peroxygen compound together with a compound according to general formula (I) is preferably used for the bleaching of stains, in particular tea, when washing textiles, in particular in an aqueous, surfactant-containing liquor. The phrase "bleaching of stains" is to be understood in its broadest sense and includes the bleaching of colored dirt present on the textile, the bleaching of colored dirt that is present in the washing liquor and has been removed from the textile, and the oxidative destruction of textile dyes that are present in the washing liquor and have been removed from textiles under the washing conditions before said textile dyes can be absorbed onto textiles of different colors.

Another preferred embodiment according to the invention is the use of a peroxygen compound together with the compound according to general formula (I) in in particular aqueous, surfactant-containing cleaning solutions for hard surfaces, in particular for dishes, for bleaching colored stains, for example tea. Here, too, the term "bleaching" is understood to mean both the bleaching of dirt present on the hard surface, in particular tea, and the bleaching of dirt that is present in the cleaning liquor, for example a dishwashing liquor, and has been removed from the hard surface.

The uses according to the invention for enhancing the cleaning performance of washing and cleaning agents and for bleaching colored stains can be realized particularly simply by introducing the compound of general formula (I) into an in particular surfactant-containing aqueous liquor which also contains the peroxygen compound and the textile to be cleaned or the object having a hard surface to be cleaned, the compound according to general formula (I), the peroxygen compound and the textile or object having a hard surface being introduced in any order, or by applying an in particular surfactant-containing aqueous liquor which contains the compound of general formula (I) and the peroxygen compound to the textile to be cleaned or the hard surface to be cleaned. The compound of general formula (I) is preferably used as a component of a washing or cleaning agent which particularly preferably also contains the peroxygen compound. The invention therefore further relates to washing or cleaning agents containing a compound according to general formula (I). A washing or cleaning agent preferably contains from 0.01 wt. % to 50 wt. %, in particular from 0.1 wt. % to 25 wt. % and particularly preferably from 1 wt. % to 10 wt. %, of a compound according to general formula (I). The percentages by weight relate to the total washing or cleaning agent; this also applies to all of the percentages by weight given below, unless expressly stated otherwise. In aqueous washing or cleaning liquors, amounts of from 1 g/L to 10 g/L, in particular from 2 g/L to 5 g/L, of such agents are preferably used. The pH of the washing and cleaning liquors is generally non-critical and can be, for example, in the range of from pH 4 to pH 14; the pH is preferably in the range of from pH 6 to pH 12, in particular from pH 7 to pH 10.

The above-mentioned preferred embodiments of the compounds according to formula (I) are also preferred for use in the methods, uses and agents according to the invention.

The compounds of formula (I) and the peracids formed therefrom under perhydrolysis conditions are generally more water-soluble than similar compounds in which the cationic substituent is absent, or which instead have an anionic substituent, and they have a higher affinity for the surface to be cleaned, especially if it consists of cotton or contains cotton.

The washing and cleaning agents according to the invention, which may be in the form of powdered solids, in further-compacted particulate form, homogeneous solutions, or suspensions or dispersions, may in principle contain, in addition to the bleach-enhancing compound used according to the invention and preferably a peroxygen compound, all known ingredients conventional in such agents. The washing and cleaning agents according to the invention may, in particular, contain builder substances, surface-active surfactants, water-miscible organic solvents, enzymes, sequestering agents, electrolytes, pH regulators and further auxiliaries such as optical brighteners, graying inhibitors, dye transfer inhibitors, foam regulators, additional peroxygen activators, and dyes and fragrances.

Suitable organic or inorganic peroxygen compounds are organic peracids or peracid salts of organic acids, such as phthalimidopercapronic acid, perbenzoic acid or salts of diperdodecanedioic acid, but in particular inorganic peroxygen compounds such as hydrogen peroxide and inorganic salts that release hydrogen peroxide under the conditions of cleaning, such as perborate, percarbonate and/or persilicate, and hydrogen peroxide inclusion compounds, such as H2O2 urea adducts. Hydrogen peroxide can also be produced by means of an enzymatic system, i.e., an oxidase and the substrate thereof. If solid peroxygen compounds are intended to be used, these may be used in the form of powders or granules, which may also be coated in a manner known in principle. The peroxygen compounds can be added to the washing or cleaning liquor as such or in the form of agents containing them, which in principle can contain all conventional washing or cleaning agent components. The use of alkali percarbonate, alkali perborate monohydrate or hydrogen peroxide in the form of aqueous solutions containing from 3 wt. % to 10 wt. % of hydrogen peroxide is particularly preferred. Here and in the following, sodium is the preferred alkali metal. If a washing or cleaning agent according to the invention contains peroxygen compounds, in particular sodium percarbonate, these compounds are preferably present in amounts of from 1 wt. % to 15 wt. %, in particular from 4 wt. % to 6 wt. %.

In particular, compounds which produce, under perhydrolysis conditions, optionally substituted perbenzoic acid and/or aliphatic peroxycarboxylic acids having 1 to 12 C atoms, in particular 2 to 4 C atoms, alone or in mixtures, can be used as a compound that yields peroxycarboxylic acid under perhydrolysis conditions. The bleach activators mentioned at the outset that have O- and/or N-acyl groups in particular of the stated number of C atoms and/or optionally substituted benzoyl groups are suitable. Preferred are polyacylated alkylenediamines, in particular tetraacetylethylenediamine (TAED), acylated glycolurils, in particular tetraacetylglycoluril (TAGU), acylated triazine derivatives, in particular 1,5-diacetyl-2,4-dioxo-hexahydro-1,3,5-triazine (DADHT), N-acylimides, in particular N-nonanoylsuccinimide (NOSI), acylated phenolsulfonates or carboxylates or the sulfonic or carboxylic acids thereof, in particular nonanoyl or isononanoyl or lauroyl oxybenzenesulfonate (NOBS or iso-NOBS or LOBS), 4-(2-decanoyloxyethoxycarbonyloxy)-benzenesulfonate (DECOB S) or decanoyloxybenzoate (DOBA), acylated polyhydric alcohols, in particular triacetin, ethylene glycol diacetate and 2,5-diacetoxy-2,5-dihydrodrofuran and acetylated sorbitol and mannitol and mixtures thereof (SORMAN), acylated sugar derivatives, in particular pentaacetylglucose (PAG), pentaacetylfructose, tetraacetylxylose and octaacetyl lactose, acetylated, optionally N-alkylated glucamine and gluconolactone, and/or N-acylated lactams, for example N-benzoyl-caprolactam. A washing or cleaning agent according to the invention preferably does not contain further compounds that yield peroxycarboxylic acid under perhydrolysis conditions.

In addition to, or instead of, the mentioned further compounds which form peroxycarboxylic acids under perhydrolysis conditions, other bleach-activating compounds, such as nitriles, from which perimidic acids are formed, may be present. These include in particular aminoacetonitrile derivatives having a quaternized nitrogen atom according to the formula

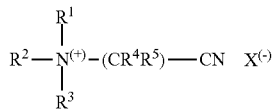

in which R1 represents —H, —CH3, a C2-24 alkyl or alkenyl functional group, a substituted C1-24 alkyl or C2-24 alkenyl functional group having at least one substituent from the group —Cl, —Br, —OH, —NH2, —CN and —N(+)—CH2—CN, an alkyl or alkenylaryl functional group having a C1-24 alkyl group, or a substituted alkyl or alkenylaryl functional group having at least one, preferably two, optionally substituted C1-24 alkyl group(s) and optionally further substituents on the aromatic ring, R2 and R3 are selected, independently of one another, from —CH2—CN, —CH3, —CH2—CH3, —CH2—CH2—CH3, —CH(CH3)—CH3, —CH2—OH, —CH2—CH2—OH, —CH(OH)—CH3, —CH2—CH2—CH2—OH, —CH2—CH(OH)—CH3, —CH(OH)—CH2—CH3, —(CH2CH2—O)nH, where n=1, 2, 3, 4, 5 or 6, R4 and R5 have, independently of one another, the meaning specified above for R1, R2 or R3, where at least 2 of the functional groups mentioned, in particular R2 and R3, also including the nitrogen atom and possibly other heteroatoms, can be linked to one another in a ring-closing manner and then preferably form a morpholino ring, and X is a charge-balancing anion, preferably selected from benzenesulfonate, toluenesulfonate, cumenesulfonate, the C9-15 alkylbenzenesulfonates, the C1-20 alkyl sulfates, the C8-22 carboxylic acid methyl ester sulfonates, sulfate, hydrogen sulfate, and mixtures thereof, may be used.

It is also possible for bleach-catalyzing transition metal complexes to be present. These are preferably selected from the cobalt, iron, copper, titanium, vanadium, manganese and ruthenium complexes. Suitable ligands in the transition metal complexes are both inorganic and organic compounds, which include, in addition to carboxylates, in particular compounds having primary, secondary and/or tertiary amine and/or alcohol functions, such as pyridine, pyridazine, pyrimidine, pyrazine, imidazole, pyrazole, triazole, 2,2'-bispyridylamine, tris-(2-pyridylmethyl)amine, 1,4,7-triazacyclononane, 1,4,7-trimethyl-1,4,7-triazacyclononane, 1,5,9-trimethyl-1,5,9-triazacyclododecane, (bis-((1-methylimidazole-2-yl)-methyl))-(2-pyridylmethyl)-amine, N,N'-(bis-(1-methylimidazole-2-yl)-methyl)-ethylenediamine, N-bis-(2-benzimidazolylmethyl) aminoethanol, 2,6-bis-(bis-(2-benzimidazolylmethyl)aminomethyl)-4-methylphenol, N,N,N',N'-tetrakis-(2-benzimidazolylmethyl)-2-hydroxy-1,3-diaminopropane, 2,6-bis-(bis-(2-pyridylmethyl)aminomethyl)-4-methylphenol, 1,3-bis-(bis-(2-benzimidazolylmethyl)aminomethyl) benzene, sorbitol, mannitol, erythritol, adonitol, inositol, lactose, and optionally substituted salens, porphins and porphyrins. The inorganic neutral ligands include in particular ammonia and water. If not all coordination sites of the transition metal central atom are occupied by neutral ligands, the complex contains further, preferably anionic, ligands, of these in particular mono- or bidentate ligands. These include in particular the halides such as fluoride, chloride, bromide and iodide, and the (NO2)— group, i.e., a nitro ligand or a nitrito ligand. The (NO2)- group may also be chelated to a transition metal or it may asymmetrically bridge or η1-O-bridge two transition metal atoms. In addition to the ligands mentioned, the transition metal complexes to be used in the activator system according to the invention may carry further, generally more simple, ligands, in particular mono- or polyvalent anion ligands. For example, nitrate, acetate, trifluoroacetate, formate, carbonate, citrate, perchlorate, and complex anions such as hexafluorophosphate are suitable. The anion ligands are intended to ensure charge balance between the transition metal central atom and the ligand system. It is also possible for oxo ligands, peroxo ligands and imino ligands to be present. In particular, such ligands can also have a bridging effect, such that polynuclear complexes are produced. In the case of bridged, binuclear complexes, the two metal atoms in the complex do not need to be the same. The use of binuclear complexes in which the two transition metal central atoms have different oxidation numbers is also possible. If anion ligands are absent or the presence of anion ligands does not result in charge balance in the complex, anionic counterions which neutralize the cationic transition metal complex are present in the transition metal complex compounds. These anionic counterions include in particular nitrate, hydroxide, hexafluorophosphate, sulfate, chlorate, perchlorate, the halides such as chloride or the anions of carboxylic acids such as formate, acetate, benzoate, citrate or oxalate. Examples of such additional transition metal complex compounds are Mn(IV)

2(μ-O)3(1,4,7-trimethyl-1,4,7-triazacyclononane)-dihexafluorophosphate, [N,N'-bis[(2-hydroxy-5-vinylphenyl)-methylene]-1,2-diamino-cyclohexane]-manganese-(111)-chloride, [N,N'-bis[(2-hydroxy-5-nitrophenyl)-methylene]-1,2-diamino-cyclohexane]-manganese-(111)-acetate, [N,N'-bis [(2-hydroxyphenyl)-methylene]-1,2-phenylendiamine]-manganese-(111)-acetate, [N,N'-bis[(2-hydroxyphenyl)-methylene]-1,2-diaminocyclohexane]-manganese-(111)-chloride, [N,N'-bis[(2-hydroxyphenyl)-methylene]-1,2-diaminoethane]-manganese-(111)-chloride, [N,N'-bis[(2-hydroxy-5-sulfonatophenyl)-methylene]-1,2-diaminoethane]-manganese-(111)-chloride, manganese oxalate, nitropentaamminecobalt(111) chloride, nitritopentaamminecobalt(111) chloride, hexaamminecobalt(111) chloride, chloropentaamminecobalt(111) chloride and the peroxo complex [(NH3)5Co-O-O-Co(NH3)5]Cl4.

The agents according to the invention can contain one or more surfactants, anionic surfactants, nonionic surfactants and mixtures thereof being particularly suitable. Suitable nonionic surfactants are in particular alkyl glycosides and ethoxylation and/or propoxylation products of alkyl glycosides or linear or branched alcohols each having 12 to 18 C atoms in the alkyl portion and 3 to 20, preferably 4 to 10, alkyl ether groups. It is also possible to use corresponding ethoxylation and/or propoxylation products of N-alkylamines, vicinal diols, fatty acid esters and fatty acid amides, which correspond to the stated long-chain alcohol derivatives with regard to the alkyl portion, and also of alkyl phenols having 5 to 12 C atoms in the alkyl functional group.

Suitable anionic surfactants are in particular soaps and those containing sulfate or sulfonate groups preferably having alkali ions as cations. Soaps that can be used are preferably the alkali salts of saturated or unsaturated fatty acids having 12 to 18 C atoms. Fatty acids of this kind may also be used in a not completely neutralized form. Sulfate-type surfactants that can be used include the salts of sulfuric acid semiesters of fatty alcohols having 12 to 18 C atoms and the sulfation products of the mentioned nonionic surfactants having a low degree of ethoxylation. Sulfonate-type surfactants that can be used include linear alkylbenzene sulfonates having 9 to 14 C atoms in the alkyl portion, alkanesulfonates having 12 to 18 C atoms, and olefin sulfonates having 12 to 18 C atoms, resulting from the reaction of corresponding monoolefins with sulfur trioxide, and alpha-sulfo fatty acid esters, resulting from the sulfonation of fatty acid methyl or ethyl esters.

Surfactants of this kind are contained in the cleaning or washing agents according to the invention in proportions of preferably from 5 wt. % to 50 wt. %, in particular from 8 wt. % to 30 wt. %, while the agents according to the invention for cleaning hard surfaces, in particular dishes, preferably contain from 0.1 wt. % to 20 wt. %, in particular from 0.2 wt. % to 5 wt. %, of surfactants.

An agent according to the invention preferably contains at least one water-soluble and/or water-insoluble, organic and/or inorganic builder. The water-soluble organic builder substances include polycarboxylic acids, in particular citric acid, saccharic acids and carboxymethyl inulins, monomeric and polymeric aminopolycarboxylic acids, in particular glycinediacetic acid, methylglycinediacetic acid, nitrilotriacetic acid, iminodisuccinates such as ethylenediamine-N,N'-disuccinic acid and hydroxyiminodisuccinate, ethylenediaminetetraacetic acid and polyaspartic acid, polyphosphonic acids, in particular aminotris(methylenephosphonic acid), ethylenediamine tetrakis(methylenephosphonic acid), lysine tetra(methylenephosphonic acid) and 1-hydroxyethane-1,1-diphosphonic acid, polymeric hydroxy compounds such as dextrin, and polymeric (poly)carboxylic acids, polycarboxylates which can be obtained in particular by oxidizing polysaccharides, polymeric acrylic acids, methacrylic acids, maleic acids, and mixed polymers thereof, which may also contain, polymerized in the polymer, small portions of polymerizable substances, without a carboxylic acid functionality. The relative average molecular mass (here and in the following: weight average) of the homopolymers of unsaturated carboxylic acids is generally between 5,000 g/mol and 200,000 g/mol, that of the copolymers between 2,000 g/mol and 200,000 g/mol, preferably from 50,000 g/mol to 120,000 g/mol, in each case based on free acid. A particularly preferred acrylic acid-maleic acid copolymer has a relative average molecular mass of from 50,000 g/mol to 100,000 g/mol. Compounds of this class which are suitable, although less preferred, are copolymers of acrylic acid or methacrylic acid with vinyl ethers, such as vinyl methyl ethers, vinyl esters, ethylene, propylene, and styrene, in which the proportion of the acid is at least 50 wt. %. It is also possible to use, as water-soluble organic builder substances, terpolymers which contain two unsaturated acids and/or the salts thereof as monomers and vinyl alcohol and/or a vinyl alcohol derivative or a carbohydrate as the third monomer. The first acid monomer or the salt thereof is derived from a monoethylenically unsaturated C3-C8 carboxylic acid and preferably from a C3-C4 monocarboxylic acid, in particular from (meth)acrylic acid. The second acid monomer or the salt thereof can be a derivative of a C4-C8 dicarboxylic acid, maleic acid being particularly preferred. The third monomeric unit is formed in this case of vinyl alcohol and/or preferably an esterified vinyl alcohol. In particular, vinyl alcohol derivatives are preferred which are an ester of short-chain carboxylic acids, for example C1-C4 carboxylic acids, with vinyl alcohol. Preferred polymers contain from 60 wt. % to 95 wt. %, in particular from 70 wt. % to 90 wt. %, of (meth)acrylic acid or (meth)acrylate, particularly preferably acrylic acid or acrylate, and maleic acid or maleate, and from 5 wt. % to 40 wt. %, preferably from 10 wt. % to 30 wt. %, of vinyl alcohol and/or vinyl acetate. Very particularly preferred are polymers in which the weight ratio of (meth)acrylic acid or (meth)acrylate to maleic acid or maleate is between 1:1 and 4:1, preferably between 2:1 and 3:1, and in particular between 2:1 and 2.5:1. Both the amounts and the weight ratios are based on the acids. The second acid monomer or the salt thereof can also be a derivative of an allylsulfonic acid which is substituted in the 2 position with an alkyl functional group, preferably with a C1-C4 alkyl functional group, or an aromatic functional group which is preferably derived from benzene or benzene derivatives. Preferred terpolymers contain from 40 wt. % to 60 wt. %, in particular from 45 to 55 wt. %, of (meth)acrylic acid or (meth)acrylate, particularly preferably acrylic acid or acrylate, from 10 wt. % to 30 wt. %, preferably from 15 wt. % to 25 wt. %, of methallyl sulfonic acid or methallyl sulfonate and, as the third monomer, from 15 wt. % to 40 wt. %, preferably from 20 wt. % to 40 wt. %, of a carbohydrate. This carbohydrate may be, for example, a mono-, di-, oligo- or polysaccharide, mono-, di- or oligosaccharides being preferred. Sucrose is particularly preferred. The use of the third monomer presumably incorporates predetermined breaking points into the polymer which are responsible for the good biodegradability of the polymer. These terpolymers generally have a relative average molecular mass between 1,000 g/mol and 200,000 g/mol, preferably between 200 g/mol and 50,000 g/mol. Further preferred copolymers are those which have acrolein and acrylic acid/acrylic acid salts or vinyl acetate as monomers. The organic builder substances may, in particular for the preparation of liquid agents, be used in the form of aqueous solutions, preferably in the form of 30 to 50 wt. % aqueous solutions. All mentioned acids are generally used in the form of the water-soluble salts thereof, in particular alkali salts thereof.

Organic builder substances of this kind can, if desired, be contained in amounts of up to 40 wt. %, in particular up to 25 wt. %, and preferably of from 1 wt. % to 8 wt. %. Amounts close to the stated upper limit are preferably used in pasty or liquid, in particular water-containing, agents.

In particular polyphosphates, preferably sodium triphosphate, are suitable as water-soluble inorganic builder materials. In particular crystalline or amorphous, water-dispersible alkali aluminosilicates are used as water-insoluble inorganic builder materials in amounts not exceeding 25 wt. %, preferably of from 3 wt. % to 20 wt. %, and in particular in amounts of from 5 wt. % to 15 wt. %. Of these, the crystalline sodium aluminosilicates of washing agent quality, particularly zeolite A, zeolite P, and zeolite MAP, and optionally zeolite X, are preferred. Amounts close to the stated upper limit are preferably used in solid, particulate agents. Suitable aluminosilicates have in particular no particles having a particle size greater than 30 μm and preferably comprise at least 80 wt. % of particles having a size smaller than 10 μm. The calcium binding capacity of said aluminosilicates is generally in the range of from 100 to 200 mg CaO per gram.

In addition or as an alternative to said water-insoluble aluminosilicate and alkali carbonate, further water-soluble inorganic builder materials may be contained. These include, in addition to the polyphosphates such as sodium triphosphate, in particular the water-soluble crystalline and/or amorphous alkali silicate builders. Water-soluble inorganic builder materials of this kind are contained in agents according to the invention preferably in amounts of from 1 wt. % to 20 wt. %, in particular from 5 wt. % to 15 wt. %. The alkali silicates that can be used as builder materials preferably have a molar ratio of alkali oxide to SiO2 of less than 0.95, in particular of from 1:1.1 to 1:12, and may be present in amorphous or crystalline form. Preferred alkali silicates are sodium silicates, in particular amorphous sodium silicates, having a Na2O:SiO2 molar ratio of from 1:2 to 1:2.8. Crystalline phyllosilicates of the general formula Na2SixO2x+1·y H2O, where x, referred to as the module, is a number from 1.9 to 4, y is a number from 0 to 20, and preferred values for x are 2, 3 or 4, are preferably used as crystalline silicates, which may be present alone or in a mixture with amorphous silicates. Preferred crystalline phyllosilicates are those in which x in the stated general formula assumes the values 2 or 3. In particular, both β- and δ-sodium disilicates (Na2Si2O5·y H2O) are preferred. Practically water-free crystalline alkali silicates of the above general formula, in which x is a number from 1.9 to 2.1 and which are produced from amorphous alkali silicates, may also be used in agents according to the invention. In a further preferred embodiment of agents according to the invention, a crystalline sodium phyllosilicate having a module of from 2 to 3, as can be prepared from sand and soda, is used. Sodium silicates having a module in the range of from 1.9 to 3.5 are used in another embodiment of agents according to the invention. In a preferred embodiment of agents according to the invention, a granular compound of alkali silicate and alkali carbonate is used, as is commercially available, for example, under the name Nabion® 15.

Automatic dishwashing detergents according to the invention are preferably low-alkaline and contain the conventional alkali carriers such as alkali silicates, alkali carbonates and/or alkali hydrogen carbonates. The conventionally used alkali carriers include carbonates, hydrogen carbonates and alkali silicates having a molar ratio SiO2/M2O (M=alkali atom) of from 1.5:1 to 2.5:1. Alkali silicates can be contained in amounts of up to 30 wt. %, based on the total agent. The use of the highly alkaline metasilicates as alkali carriers is preferably dispensed with entirely. The alkali carrier system preferably used in the agents according to the invention is a mixture of carbonate and hydrogen carbonate, preferably sodium carbonate and sodium hydrogen carbonate, which is contained in an amount of up to 60 wt. %, preferably of from 10 wt. % to 40 wt. %. Depending on which pH value is ultimately desired, the ratio of carbonate and hydrogen carbonate used varies, but usually sodium hydrogen carbonate is used in excess, and therefore the weight ratio between hydrogen carbonate and carbonate is generally from 1:1 to 15:1.

In a further embodiment of agents according to the invention for cleaning dishes, said agents contain from 20 wt. % to 40 wt. % of water-soluble organic builders, in particular alkali citrate, from 5 wt. % to 15 wt. % of alkali carbonate and from 20 wt. % to 40 wt. % of alkali disilicate.

Enzymes in particular from the class of proteases, lipases, cutinases, amylases, pullulanases, xylanases, hemicellulases, cellulases, peroxidases and oxidases and mixtures thereof are suitable as enzymes optionally contained in the agents according to the invention, with the use of proteases, amylases, lipases and/or celluases being particularly preferred. The proportion is preferably from 0.2 wt. % to 1.5 wt. %, in particular from 0.5 wt. % to 1 wt. %. The enzymes can be adsorbed on carrier substances, as is conventional, and/or embedded in coating substances or incorporated as concentrated liquid formulations which are as anhydrous as possible.

Suitable graying inhibitors or soil release active ingredients are cellulose ethers, such as carboxymethyl cellulose, methyl cellulose, hydroxyalkyl celluloses and mixed cellulose ethers, such as methyl hydroxyethyl cellulose, methyl hydroxypropyl cellulose and methyl carboxymethyl cellulose. Sodium carboxymethyl cellulose and mixtures thereof with methyl cellulose are preferably used. The soil release active ingredients conventionally used include copolyesters which contain dicarboxylic acid units, alkylene glycol units and polyalkylene glycol units. The proportion of graying inhibitors and/or soil release active ingredients in agents according to the invention is generally no greater than 2 wt. % and is preferably from 0.5 wt. % to 1.5 wt. %.

Derivatives of diaminostilbene disulfonic acid or the alkali metal salts thereof, for example, can be contained as optical brighteners for in particular textiles made of cellulose fibers (for example cotton). Salts of 4,4'-bis(2-anilino-4-morpholino-1,3,5-triazinyl-6-amino)stilbene-2,2'-disulfonic acid or compounds having a similar structure which, instead of the morpholino group, have a diethanolamino group, a methylamino group, or a 2-methoxyethylamino group are suitable, for example. Furthermore, brighteners of the substituted 4,4'-distyryl-di-phenyl type may also be present, for example 4,4'-bis(4-chloro-3-sulfostyryl)-diphenyl. Mixtures of brighteners can also be used. Brighteners of the 1,3-diaryl-2-pyrazoline type, for example 1-(p-sulfoamoylphenyl)-3-(p-chlorophenyl)-2-pyrazoline, and compounds having a similar structure, are particularly suitable for polyamide fibers. The optical brightener or brightener mixture content in the agent is generally no greater than 1 wt. %, preferably from 0.05 wt. % to 0.5 wt. %. In a preferred embodiment of the invention, the agent does not contain any active ingredients of this type.

The conventional foam regulators that can be used in the agents according to the invention include, for example, mixtures of polysiloxane and silicic acid, the fine-particle silicic acid contained therein preferably being silanized or otherwise hydrophobized. The polysiloxanes can consist of both linear compounds and crosslinked polysiloxane resins, as well as mixtures thereof. Other defoamers are paraffinic hydrocarbons, in particular micro-paraffins and paraffin waxes of which the melting point is above 40° C., saturated fatty acids or soaps having in particular 20 to 22 C atoms, for example sodium behenate, and alkali salts of phosphoric acid mono- and/or dialkyl esters in which the alkyl chains each have 12 to 22 C atoms. Among these, sodium mono-alkyl phosphate and/or sodium dialkyl phosphate having C16 to C18 alkyl groups is preferably used. The proportion of foam regulators can preferably be from 0.2 wt. % to 2 wt. %.

The organic solvents that can be used in the agents according to the invention, in particular when said agents are present in liquid or pasty form, include alcohols having 1 to 4 C atoms, in particular methanol, ethanol, isopropanol, and tert-butanol, diols having 2 to 4 C atoms, in particular ethylene glycol and propylene glycol, and mixtures thereof, and the ethers that are derivable from the mentioned compound classes. Water-miscible solvents of this kind are present in agents according to the invention in amounts of preferably no greater than 20 wt. %, in particular from 1 wt. % to 15 wt. %.

In order to set a desired pH that does not result automatically from mixing the other components, the agents according to the invention can contain acids that are compatible with the system and environment, in particular citric acid, acetic acid, tartaric acid, malic acid, lactic acid, glycolic acid, succinic acid, glutaric acid, and/or adipic acid, but also mineral acids, in particular sulfuric acid or alkali hydrogen sulfates, or bases, in particular ammonium or alkali hydroxides. pH regulators of this kind are contained in the agents according to the invention preferably in amounts of no greater than 10 wt. %, in particular from 0.5 wt. % to 6 wt. %.

The preparation of the solid agents according to the invention presents no difficulties, and can be carried out in principle in a known manner, for example by spray drying or granulation, a peroxygen compound and a bleach catalyst optionally being added separately later.

Agents according to the invention in the form of solutions containing aqueous solvents or other conventional solvents are particularly advantageously prepared by simple mixing of the ingredients, which can be put into an automatic mixer in bulk or as a solution.

The agents according to the invention are preferably in the form of powdered, granular or tablet-like preparations, which can be prepared in a manner known per se, for example by mixing, granulation, roll compaction and/or by spray drying the thermally loadable components and mixing in the more sensitive components, including in particular enzymes, bleaching agents and bleach activating compounds. For the production of agents according to the invention having an increased bulk weight, in particular in the range of from 650 g/L to 950 g/L, a method having an extrusion step is preferred.

To prepare agents in tablet form, the procedure is preferably such that all components are mixed with one another in a mixer, and the mixture is compressed using conventional tablet presses, such as eccentric presses or rotary presses, using pressures in the range of from 200·105 Pa to 1,500·105 Pa. This readily produces break-resistant tablets that nonetheless dissolve sufficiently quickly under usage conditions, with flexural strengths of normally above 150 N. A tablet produced in this way preferably has a weight of from 15 g to 40 g, in particular from 20 g to 30 g, with a diameter of from 35 mm to 40 mm.

The preparation of agents according to the invention in the form of non-dust-forming, storage-stable, free-flowing powders and/or granules with high bulk densities in the range of from 800 g/L to 1,000 g/L can also be carried out in that, in a first stage of the method, the builder components are mixed with at least one proportion of liquid mixture components to increase the bulk density of this premix and then—if desired after intermediate drying—the other components of the agent, including the performance-enhancing active ingredient or the performance-enhancing active ingredient combination, are combined with the premix obtained in this way.

EXAMPLES

Example 1

Preparation of Bleach-Enhancing Compounds a) Preparation of N,N,N-Triethyl-N-(4-((2-Oxoazepan-1-Yl)Carbonyl)Phenyl)Ethanaminium Chloride (Not Part of the Invention) (G. Wang, G. de Aragano Umbuzeiro, J. Aparecida Vendemiatti, A. Caloto de Oliveira, F. Inforcato Vacchi, M. Hussain, P. J. Hauser, H. S. Freeman, D. Hinks, J. Surfact. Deterg. 20 (2017), 277-285; S-H. Lim, N.Ç. Gürsoy, P. Hauser, D. Hinks, Color. Technol. 120 (2004), 114-118)

a) i): A solution of 37.6 g of 4-chloromethyl benzoyl chloride (199 mmol) in 20 ml of toluene was added in drops to a solution, heated to boiling under reflux under a N2 atmosphere, of 22.5 g of caprolactam (199 mmol) and 30.4 g of triethylamine (1.5 equivalents) in 250 ml of toluene. The reaction mixture was heated to boiling under reflux with stirring for 6 hours, and then left to cool to room temperature and filtered. The filtrate was stored in the refrigerator for 12 hours, and the precipitate was filtered off, washed with 5% aqueous NaHCO3 solution and dried at 40° C. for 12 hours. 47.6 g (179 mmol; 90%) of 1-((4-(chloromethyl)phenyl)carbonyl) azepan-2-one was obtained as a colorless solid.
$^1$H-NMR (400 MHz, DMSO-d6): δ=1.85 (bs, 6H), 2.67-2.73 (m, 2H), 3.94-4.01 (m, 2H), 4.59 (s, 2H), 7.41 (pd, J=8.5 Hz, 2H), 7.53 (pd, J=8.5 Hz, 2H) ppm.

a) ii): A solution of 24.1 g of triethylamine (240 mmol) in 10 ml of acetonitrile was added in drops to a solution of 60 g of ((4-(chloromethyl)phenyl)carbonyl)azepan-2-one (230 mmol) prepared according to a) i) in 350 ml of acetonitrile, under a N2 atmosphere and over the course of 1 hour, and the reaction mixture was heated to boiling under reflux with stirring for 4 hours. Said mixture was then cooled to room temperature and the solvent was removed on a rotary evaporator. 40 ml of acetone was added to the residue, the mixture was heated to 50-60° C. for 1 hour, then the acetone was removed by filtration, and the process was repeated three times. Finally, the residue was dried at 40° C. overnight. 58.9 g (161 mmol; 72%) of N,N,N-triethyl-N-(4-((2-oxoazepan-1-yl)carbonyl)phenyl) ethanaminium chloride was obtained as a colorless powder.

$^1$H-NMR (400 MHz, CDCl3): δ=1.37 (t, J=7.2 Hz, 9H), 1.74-1.85 (bs, 6H), 2.60-2.68 (m, 2H), 3.35 (q, J=7.2 Hz, 6H), 3.92 (bs, 2H), 4.82 (s, 2H), 7.47 (pd, J=8.4 Hz, 2H), 7.63 (pd, J=8.4 Hz, 2H) ppm.

b) Preparation of 4-Methyl-4-(4-((2-Oxoazepan-1-Yl)Carbonyl)Benzyl)Morpholin-4-Ium Chloride A solution of 28 g N-methylmorpholine (280 mmol) in 50 ml of acetonitrile was added in drops to a solution of 70 g of 1-((4-(chloromethyl)phenyl)carbonyl)azepan-2-one (260 mmol) prepared according to a) i) in 350 ml of acetonitrile, under a N2 atmosphere, and the reaction mixture was heated to boiling under reflux with stirring for 4 hours. Said mixture was then cooled to room temperature and the solvent was removed on a rotary evaporator. 40 ml of acetone was added to the residue, the mixture was heated to 50-60° C. for 1 hour, then the acetone was removed by filtration, and the process was repeated three times. Finally, the residue was dried at 40° C. overnight. 79.1 g (216 mmol; 82%) of 4-methyl-4-(4-((2-oxoazepan-1-yl)carbonyl)benzyl)morpholin-4-ium chloride was obtained as a colorless solid.

c) Preparation of 4-Methyl-4-(4-((2-Oxopyrrolidin-L-Yl)Carbonyl)Benzyl)Morpholin-4-Ium Chloride c) i): A solution of 75.6 g of 4-chloromethyl benzoyl chloride (400 mmol) in 50 ml of toluene was added in drops to a solution, heated to boiling under reflux under a N2 atmosphere, of 34 g of 2 oxopyrrolidine (400 mmol) and 60.7 g of triethylamine (1.5 equivalents) in 450 ml of toluene. The reaction mixture was heated to boiling under reflux with stirring for 6 hours, and then left to cool to room temperature and filtered. The filtrate was stored in the refrigerator for 12 hours, and the precipitate was filtered off, washed with 5% aqueous NaHCO3 solution and dried at 40° C. for 12 hours. 79.1.8 g (332 mmol; 83%) of 1-((4-(chloromethyl)phenyl)carbonyl)pyrrolidin-2-one was obtained as a colorless solid.

$^1$H-NMR (400 MHz, DMSO-d6): δ=1.75-1.95 (m, 4H, CH2), 3.60-3.80 (m, 2H, CH2), 4.81 (s, 2H, CH2), 7.41-7.49 (m, 2H, Ar-H), 7.51-7.59 (m, 2H, Ar-H) ppm.

c) ii) A solution of 10.1 g of 1-N-methylmorpholine (100 mmol) in 25 ml of acetonitrile was added in drops to a solution of 22.7 g of 1-((4-(chloromethyl)phenyl)carbonyl)pyrrolidin-2-one (95 mmol) prepared according to c) i) in 125 ml of acetonitrile, under a N2 atmosphere, and the reaction mixture was heated to boiling with reflux with stirring for 4 hours. Said mixture was then cooled to room temperature and the solvent was removed on a rotary evaporator. 40 ml of acetone was added to the residue, the mixture was heated to 50-60° C. for 1 hour, then the acetone was removed by filtration, and the process was repeated three times. Finally, the residue was dried at 40° C. overnight. 25.6 g (79.8 mmol; 84%) of 4-methyl-4-(4-((2-oxopyrrolidin-1-yl)carbonyl)benzyl)morpholin-4-ium chloride was obtained as a colorless solid.

FTIR (film): ṽ=2966, 2889, 1734, 1661, 1480, 1415, 1358, 1300, 1245, 1189, 1114, 1065, 1019, 896, 862, 829, 750, 733, 631, 611, 553 cm$^{-1}$.

$^1$H-NMR (400 MHz, CDCl3): δ=2.06 (m, 2H), 2.54 (t, J=4.0 Hz, 2H), 3.35 (s, 3H), 3.59 (d, J=12.9 Hz, 2H), 3.70-3.80 (m, 2H), 3.84-4.03 (m, 4H), 3.89 (t, J=7.1 Hz, 2H), 5.36 (s, 2H), 7.52 (pd, J=8.3 Hz, 2H), 7.75 (pd, J=8.3 Hz, 2H) ppm.

$^{13}$C-NMR (100.6 MHz, D2O): δ =19.8 (t), 35.9 (t), 48.5 (q), 49.9 (t), 62.1 (t), 63.2 (t), 71.6 (t), 131.7 (d, 2C), 132.4 (s), 135.8 (d, 2C), 139.3 (s), 174.5 (s), 181.9 (s).

MS (ESI positive mode, +3.5 kV): 234 (9%), 303 ([M-Cl-]$^+$, 100%).

Example 2

Discoloration Test 98 mg of sodium percarbonate and 13.1 mg of TAED or one of the compounds prepared in Examples 1 a) or 1 b) were added to a solution of 2.5 mg of morin in 100 ml of water, adjusted to pH 10-11 by adding NaOH, and stirred at room temperature. The time taken for the yellow color to completely disappear was determined and is shown in Table 1.

TABLE 1

| Time to complete discoloration | |
|---|---|
| Active ingredient | Duration [minutes] |
| TAED | 420 |
| Compound from Example 1 a) | 270 |
| Compound from Example 1 b) | 240 |
| Compound from Example 1 c) | 305 |

Example 3

Washing Tests

Washing tests were carried out at 30° C. with standardized stains on cotton as specified in Table 3, using a washing liquor containing 3.8 g/L of a solid washing agent of the composition specified in Table 2 below, with agents M1 and M2 containing the compounds according to the invention as prepared in Example 1 b) and c) and, for comparison, agent V2 containing the compound from Example 1 a) which is not part of the invention and agent V1 not containing any such compound, but rather the conventional bleach activator TAED The evaluation was carried out by measuring color distance according to the L*a*b* values and the Y values calculated therefrom as a measure of brightness. Table 3 shows the differences in the Y values achieved after washing between V1 and M1, V1 and M2 and V1 and V2.

TABLE 2

| | Composition (wt. %) | | | |
|---|---|---|---|---|
| | V1 | M1 | M2 | V2 |
| Na alkylbenzene sulfonate | 13 | 13 | 13 | 13 |
| Na fatty alcohol sulfate | 3 | 3 | 3 | 3 |
| Na carboxymethyl cellulose | 3 | 3 | 3 | 3 |
| HEDP-Na4 | 1 | 1 | 1 | 1 |
| Na polyacrylate | 3 | 3 | 3 | 3 |
| Sodium silicate | 7 | 7 | 7 | 7 |
| Sodium carbonate | 21 | 21 | 21 | 21 |
| Sodium hydrogen carbonate | 10 | 10 | 10 | 10 |
| Sodium percarbonate | 12 | 12 | 12 | 12 |
| TAED | 3.1 | — | — | — |
| Compound from Example 1 c) | — | 3.1 | — | — |
| Compound from Example 1 b) | — | — | 3.1 | — |
| Compound from Example 1 a) | — | — | — | 3.1 |
| Water, sodium sulfate, perfume dye to make up to 100 | | | | |

TABLE 3

| | ΔY values | | |
|---|---|---|---|
| | Agent | | |
| Stain | M1 | M2 | V2 |
| Red wine | 3.9 | 4.5 | ND |
| Coffee | 2.3 | 3.4 | ND |
| Beetroot | 2.7 | 2.6 | ND |
| Tea | 2.4 | 1.8 | 1.5 |
| Cherry juice | 2.4 | 2.0 | ND |
| Apple | 1.8 | 1.7 | 1.0 |

ND: not determined

The brightness values when the active ingredients essential to the invention are used are greater than those produced when the washing agents containing other bleach activators are used.

Example 4

Cleaning Tests 0.5 g of a mixture of lactose and ovalbumin (weight ratio 3:1) was stirred in 10 ml of water at room temperature for 10 minutes, and then the mixture was freeze-dried, ground in a mortar and heated to 160° C. for 20 minutes. Mixtures of 15 mg of the burnt-on stain simulating food residue obtained in this way, 3.75 mg of sodium percarbonate and 0.5 mg of a compound prepared in Example 1 a), 1 b) or 1 c) in 5 ml of water were heated to 60° C. for 48 hours in a mechanical shaker. After the durations specified in Table 4, the dissolution of the artificial stain was visually evaluated and rated on a scale from 0 (no dissolution) to ++++ (completely dissolved).

TABLE 4

| | Dissolution of burnt-on stain | | | | | | |
|---|---|---|---|---|---|---|---|
| | Duration | | | | | | |
| Active ingredient | 0.5 h | 1 h | 2 h | 4 h | 6 h | 24 h | 48 h |
| None | 0 | 0 | 0 | 0 | 0 | 0 | 0 |
| Compound from Example 1 b) | + | + | ++ | +++ | +++ | +++ | ++++ |
| Compound from Example 1 c) | + | + | ++ | +++ | +++ | +++ | ++++ |
| Compound from Example 1 a) | 0 | 0 | + | + | + | + | ++ |

Example 5

Additional Cleaning Test

Dishes provided with the standardized stains specified in Table 5 below were rinsed in a Miele® GSL2 dishwasher in the 45 8 55 program, using water having a water hardness of 21° dH and a dishwashing tablet which contained sodium percarbonate and did not contain any bleach activators or catalysts and to which, for comparison, 0.4 g TAED (agent V3) or 0.59 g of the compound from Example 1 a) (agent V4), or 0.55 g of the compound from Example 1 c) (agent M3) or 0.58 g of the compound from Example 1 b) (agent M4) had been added. The stain removal performance was visually assessed by trained observers and rated on a scale from 0 (=heavily stained) to 10 (=° completely clean) using the comparative images published in SÖFW-Journal 132, 2006, 35-49. The scores also specified in Table 5 were achieved for the agents containing the bleach activators in approximately the same molar amount.

TABLE 5

| | Cleaning scores | | | | | |
|---|---|---|---|---|---|---|
| | Stain | | | | | |
| Agent | Tea (Assam) | Tea (BOP) | Creme brûlée | Burnt-on ground meat | Egg yolk | Starch |
| V3 | 2.0 | 2.0 | 6.6 | 4.8 | 3.2 | 5.9 |
| V4 | 6.2 | 6.7 | 6.5 | 5.6 | 3.1 | 6.2 |
| M3 | 7.2 | 7.0 | 7.0 | 5.3 | ND | 6.6 |
| N4 | 6.8 | ND | ND | 6.0 | 3.4 | ND |

ND: not determined

It can be seen that the agents containing the active ingredients according to the invention performed better than the agents tested for comparison purposes.

What is claimed is:

1. A bleach-activating compound of general formula (I)

$$\text{(I)}$$

in which

A represents O, S or Se;

Z represents an optionally substituted C1-30 alkylene, C3-30 cycloalkylene, arylene, alkylenearylene or arylenealkylene functional group;

$X^-$ represents an anion;

Y represents $NR^6$, O, S or Se;

R, $R^1$, $R^2$, $R^3$, $R^4$, $R^5$ and $R^6$ represent, independently of one another, H, a $C_{1-30}$ alkyl, $C_{3-30}$ cycloalkyl, aryl, alkylaryl or arylalkyl functional group; and n represents a number in the range of from 1 to 12, wherein, in the hydrocarbon functional groups, 1 or more non-adjacent carbon atoms not bonded to a heteroatom can be replaced by a heteroatom.

2. The bleach-activating compound of claim 1, wherein the anion $X^-$ is selected from the group consisting of chloride, bromide, iodide, tosylate, mesylate, triflate, sulfate, carbonate, and phosphate.

3. The bleach-activating compound of claim 1, wherein in the hydrocarbon functional groups 1 or more non-adjacent carbon atoms not bonded to a heteroatom can be replaced by N, O, S and/or Se.

4. The bleach-activating compound of claim 1, wherein the compound of general formula (I) corresponds to the general formula (II)

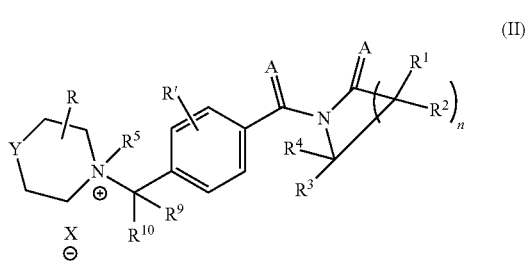

in which R', $R^9$ and $R^{10}$ represent, independently of one another, H, a $C_{1-30}$ alkyl, $C_{3-30}$ cycloalkyl, aryl, alkylaryl or arylalkyl functional group, it being possible, in these functional groups, to replace 1 or more non-adjacent carbon atoms not bonded to a heteroatom with a heteroatom.

5. A method for washing laundry or for cleaning a hard surface, comprising the steps of:
(a) providing an aqueous liquor including H2O2 or an inorganic peroxygen compound which yields $H_2O_2$ in water, and a compound according to general formula (I)

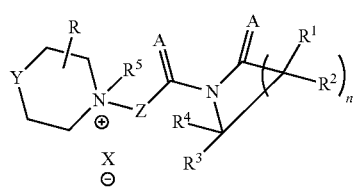

in which
A represents O, S or Se;
Z represents an optionally substituted $C_{1-30}$ alkylene, $C_{3-30}$ cycloalkylene, arylene, alkylenearylene or arylenealkylene functional group;
$X^-$ represents an anion;
Y represents $NR^6$, O, S or Se;
R, $R^1$, $R^2$, $R^3$, $R^4$, $R^5$ and $R^6$ represent, independently of one another, H, a $C_{1-30}$ alkyl, $C_{3-30}$ cycloalkyl, aryl, alkylaryl or arylalkyl functional group; and
n represents a number in the range of from 1 to 12;
wherein, in the hydrocarbon functional groups, 1 or more non-adjacent carbon atoms not bonded to a heteroatom can be replaced by a heteroatom, and
(b) bringing this liquor into contact with a textile to be washed or a hard surface to be cleaned.

6. The method according to claim 5, wherein the anion $X^-$ is selected from the group consisting of chloride, bromide, iodide, tosylate, mesylate, triflate, sulfate, carbonate, and phosphate.

7. The method according to claim 5, wherein in the hydrocarbon functional groups 1 or more non-adjacent carbon atoms not bonded to a heteroatom can be replaced by N, O, S and/or Se.

8. The method according to claim 5, wherein the contact between the aqueous liquor and the textile to be washed or the hard surface to be cleaned is made at temperatures in the range of 20° C. to 40° C.

9. The method according to claim 5, wherein the contact between the aqueous liquor and the textile to be washed or the hard surface to be cleaned is made at temperatures in the range of 20° C. to 30° C.

10. The method according to claim 5, wherein the textile to be washed or the hard surface to be cleaned remains in contact with the aqueous liquor over a period of 20 minutes to 120 minutes.

11. The method according to claim 5, wherein the textile to be washed or the hard surface to be cleaned remains in contact with the aqueous liquor over a period of 30 minutes to 90 minutes.

12. The method according to claim 5, wherein the compound of general formula (I) corresponds to the general formula (II)

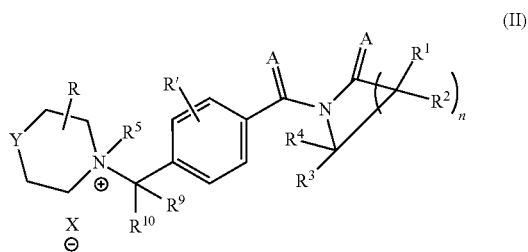

in which R', $R^9$ and $R^{10}$ represent, independently of one another, H, a $C_{1-30}$ alkyl, $C_{3-30}$ cycloalkyl, aryl, alkylaryl or arylalkyl functional group, it being possible, in these functional groups, to replace 1 or more non-adjacent carbon atoms not bonded to a heteroatom with a heteroatom.

13. The method according to claim 5, wherein the amounts of H2O2 or peroxygen compounds are selected such that the liquor comprises 10 ppm to 10% active oxygen.

14. The method according to claim 5, wherein the amount of $H_2O_2$ or peroxygen compounds are selected such that the liquor comprises 50 ppm to 5,000 ppm active oxygen.

15. A washing or cleaning agent containing a compound according to general formula (I)

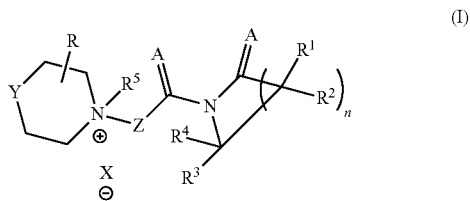

in which
A represents O, S or Se;
Z represents an optionally substituted $C_{1-30}$ alkylene, $C_{3-30}$ cycloalkylene, arylene, alkylenearylene or arylenealkylene functional group;
$X^-$ represents an anion;
Y represents $NR^6$, O, S or Se;
R, $R^1$, $R^2$, $R^3$, $R^4$, $R^5$ and $R^6$ represent, independently of one another, H, a $C_{1-30}$ alkyl, $C_{3-30}$ cycloalkyl, aryl, alkylaryl or arylalkyl functional group; and
n represents a number in the range of from 1 to 12;
wherein, in the hydrocarbon functional groups, 1 or more non-adjacent carbon atoms not bonded to a heteroatom can be replaced by a heteroatom.

16. The washing agent or cleaning agent according to claim 15, wherein the anion $X^-$ is selected from the group consisting of chloride, bromide, iodide, tosylate, mesylate, triflate, sulfate, carbonate, and phosphate.

17. The washing agent or cleaning agent according to claim 15, wherein in the hydrocarbon functional groups 1 or more non-adjacent carbon atoms not bonded to a heteroatom can be replaced by N, O, S and/or Se.

18. The washing agent or cleaning agent according to claim 15, wherein the agent includes 0.01 wt. % to 50 wt. %, of the compound according to general formula (I).

19. The washing agent or cleaning agent according to claim 15, wherein the agent includes 0.1 wt. % to 25 wt. % of the compound according to general formula (I).

20. The washing agent or cleaning agent according to claim 15, wherein the compound of general formula (I) corresponds to the general formula (II)

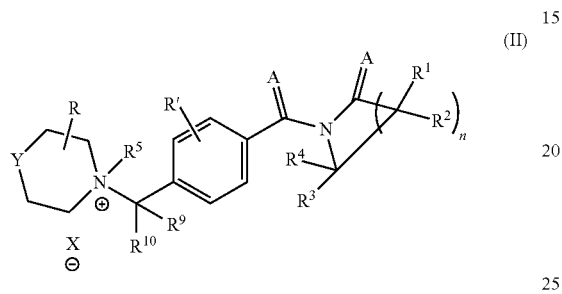

(II)

in which R', $R^9$ and $R^{10}$ represent, independently of one another, H, a $C_{1-30}$ alkyl, $C_{3-30}$ cycloalkyl, aryl, alkylaryl or arylalkyl functional group, it being possible, in these functional groups, to replace 1 or more non-adjacent carbon atoms not bonded to a heteroatom with a heteroatom in these functional groups.

* * * * *

UNITED STATES PATENT AND TRADEMARK OFFICE
CERTIFICATE OF CORRECTION

PATENT NO. : 11,767,493 B2
APPLICATION NO. : 17/749520
DATED : September 26, 2023
INVENTOR(S) : Sascha Schaefer et al.

It is certified that error appears in the above-identified patent and that said Letters Patent is hereby corrected as shown below:

In the Specification

Column 5, Line 25 change "(DECOB S)" to --(DECOBS)--.
Column 13, Line 63 change "6 = 19.8" to --$\delta$ = 19.8--.

In the Claims

Column 16, Line 41 change "C1-30" to --$C_{1-30}$--.
Column 16, Line 42 change "C3-30" to --$C_{3-30}$--.
Column 17, Line 20 change "H2O2" to --$H_2O_2$--.
Column 18, Line 32 change "H2O2" to --$H_2O_2$--.

Signed and Sealed this
Sixteenth Day of July, 2024

Katherine Kelly Vidal
*Director of the United States Patent and Trademark Office*